US011013687B1

(12) United States Patent
Vega

(10) Patent No.: US 11,013,687 B1
(45) Date of Patent: May 25, 2021

(54) PREVENTIVE AND THERAPEUTIC TREATMENT FOR COVID 19 AND ANY OTHER DISEASE CAUSED BY SARS COV 2

(71) Applicant: Amcyte Pharma, Inc., Boston, MA (US)

(72) Inventor: Julio César Vega, Buenos Aires (AR)

(73) Assignee: Amcyte Pharma, Inc., Boston, MA (US)

( * ) Notice: Subject to any disclaimer, the term of this patent is extended or adjusted under 35 U.S.C. 154(b) by 0 days.

(21) Appl. No.: 16/900,488

(22) Filed: Jun. 12, 2020

Related U.S. Application Data

(60) Provisional application No. 63/035,982, filed on Jun. 8, 2020.

(51) Int. Cl.
| | | |
|---|---|---|
| *A61K 9/00* | (2006.01) | |
| *A61K 9/08* | (2006.01) | |
| *A61K 47/10* | (2017.01) | |
| *A61K 31/047* | (2006.01) | |
| *A61K 47/02* | (2006.01) | |
| *A61K 31/731* | (2006.01) | |

(52) U.S. Cl.
CPC .......... *A61K 9/0078* (2013.01); *A61K 9/0043* (2013.01); *A61K 9/08* (2013.01); *A61K 31/047* (2013.01); *A61K 31/731* (2013.01); *A61K 47/02* (2013.01); *A61K 47/10* (2013.01)

(58) Field of Classification Search
CPC .......... A61K 9/00; A61K 31/14; A61K 45/06
See application file for complete search history.

(56) References Cited

U.S. PATENT DOCUMENTS

| | | | | |
|---|---|---|---|---|
| 6,599,883 B1 * | 7/2003 | Romeo | ................ | A61K 9/0043 514/738 |
| 8,512,682 B2 * | 8/2013 | Brisley | ................... | A23L 33/40 424/49 |
| 2008/0319087 A1 * | 12/2008 | Esperester | .............. | A61P 31/14 514/655 |

FOREIGN PATENT DOCUMENTS

| | | | | |
|---|---|---|---|---|
| CA | 2992352 A1 | 1/2017 | | |
| WO | WO-2017009351 A1 * | 1/2017 | ........... | A61K 31/731 |

OTHER PUBLICATIONS

World Health Organization, Novel Coronavirus (2019-nCoV), Situation Report—22 (Year: 2020).*
Bitter et al., "Nasal Drug Delivery in Humans," Curr Probl Dermatol., Section II: Topical Treatment of Impaired Mucosal Membranes, 40:20-35, 2011.
Furci et al., "Inhibition of HIV-1 Infection by Human α-Defensin-5, a Natural Antimicrobial Peptide Expressed in the Genital and Intestinal Mucosae," Plos One, 7:9 pp. 1-10, 2012.
Gizurarson, "Anatomical and Histological Factors Affecting Intranasal Drug and Vaccine Delivery," Current Drug Delivery, vol. 9, pp. 566-582, 2012.
Leibbrandt et al., "Iota-Carrageenan is a Potent Inhibitor of Influenza a Virus Infection," Plos One, 5:12, pp. 1-11, 2010.
Ludwig et al., "Efficacy of a Carrageenan Nasal Spray in Patients with Common Cold: A Randomized Controlled Trial," Respiratory Research, 14:124, pp. 1-11, 2013.
Moffa et al., "Nasal Delivery Devices: A Comparative Study on Cadaver Model," BioMed Research International, vol. 2019, 6 pages, 2019.
Pires et al., "Intranasal Drug Delivery: How, Why and What For," J Pharm Pharmaceut Sci, 12(3), 288-311, 2009.
Weissman et al., "Xylitol Nasal Irrigation in the Management of Chronic Rhinosinusitis: A Pilot Study," Laryngoscope, 121, 2468-2472, 2011.
Ling et al., "Ameliorating Effect of Dietary Xylitol on Human Respiratory Syncytial Virus (hRSV) Infection," Biol. Pharm. Bull, 39, 540-546, 2016.
Yang et al., "COVID-19: A New Challenge for Human Beings," Cellular & Molecular Immunology, 2 pages, 2020.
Young et al., "Protective Effect of Dietary Xylitol on Influenza A Virus Infection," Plos One, 9:1, pp. 1-7, 2014.
Wagenmann et al., "Anatomic and Physiologic Considerations in Sinusitis," Sinusitis Anatomey and Physiology, vol. 90, pp. 419-423,1992.
Durairaj et al. (Sep. 16, 2004) "Safety Assessment of Inhaled Xylitol in Mice and Healthy Volunteers", Respiratory Research, Article No. 13, 5:10 pages.
Garcia et al. (2009) "Dosimetry of Nasal Uptake of Water-Soluble and Reactive Gases: A First Study of Interhuman Variability", Inhalation Toxicology, 21(7):607-618.
Graf et al. (Jul. 4, 2018) "Development of a Nasal Spray Containing Xylometazoline Hydrochloride and Iota-Carrageenan for the Symptomatic Relief of Nasal Congestion Caused by Rhinitis and Sinusitis", International Journal of General Medicine, 11:275-283.
Hebar et al. (Apr. 13, 2015) "Non-Clinical Safety Evaluation of Intranasal Iota-Carrageenan", Plos One, e0122911,10(4):16 pages.
Helassa et al. (Nov. 14, 2014) "A Novel Fluorescent Sensor Protein for Detecting Changes in Airway Surface Liquid Glucose Concentration", Biochemical Journal, 464(2):213-220.
Klotman et al. (Jun. 1, 2006) "Defensins in Innate Antiviral Immunity", Nature Reviews Immunology, 6:447-456.

* cited by examiner

*Primary Examiner* — Micah Paul Young
(74) *Attorney, Agent, or Firm* — Mintz Levin Cohn Ferris Glovsky and Popeo, P.C.; Nicholas A. Zachariades

(57) ABSTRACT

Novel preventive treatment for COVID 19 and therapeutic treatment for early stages of COVID 19 or any other disease caused by SARS CoV 2. Pharmaceutical formulations and devices are disclosed to be able to implement these treatments. These treatments to prevent and alleviate the symptoms at early stages of COVID 19, the pandemic disease caused by SARS CoV 2. These treatments are based on the administration the nasal cavity and/or the lungs of solutions containing iota Carrageenan with or without the addition of xylitol as antiviral drug substances.

14 Claims, 2 Drawing Sheets

PREVENTIVE AND THERAPEUTIC TREATMENT FOR COVID 19 AND ANY OTHER DISEASE CAUSED BY SARS COV 2

CROSS REFERENCE TO RELATED APPLICATIONS

This Application claims the benefit of U.S. Provisional Application No. 63/035,982 filed on Jun. 8, 2020 as. The entire contents of this application is incorporated herein by reference in its entirety.

TECHNICAL FIELD

The present disclosure relates to a preventive treatment of diseases caused by SARS CoV 2, such as pandemic COVID 19, and a therapeutic treatment that may alleviate symptoms of this disease at early stages thereof. Nasal and inhalation formulations and devices to implement these treatments are disclosed.

BACKGROUND

Coronaviruses are enveloped, positive-sense single-stranded RNA viruses. They have the largest genomes (26-32 kb) among known RNA viruses, and are phylogenetically divided into four genera (a, (3, y, 6), with beta coronaviruses further subdivided into four lineages (A, B, C, D). Coronaviruses infect a wide range of avian and mammalian species, including humans. Of the six known human coronaviruses, four of them (HCoV-OC43, HCoV-229E, HCoV-HKU1 and HCoV-NL63) circulate annually in humans and generally cause mild respiratory diseases, although severity can be greater in infants, elderly, and the immunocompromised. In contrast, the Middle East respiratory syndrome coronavirus (MERS-CoV) and the severe acute respiratory syndrome coronavirus (SARS-CoV), belonging to beta coronavirus lineages C and B, respectively, are highly pathogenic. Both viruses emerged into the human population from animal reservoirs within the last 15 years and caused outbreaks with high case-fatality rates.

SARS CoV 2 is the virus responsible for COVID 19, the pandemic disease initiated in Wuhan, China. It provokes severe acute respiratory syndromes, that may lead to death (Yang et al., *Cellular & Molecular Immunology*; doi.org/10.1038/s41423-020-0407-x). The high pathogenicity and airborne transmissibility of SARS-CoV and MERS-CoV, the high case-fatality rate, vaguely defined epidemiology, and absence of prophylactic or therapeutic measures against coronaviruses have created an urgent need for an effective vaccine and related therapeutic agents.

SUMMARY

There is an urgent unmet need to provide an easy-to-produce medicine to prevent transmission and provide early treatment of a coronavirus, for example, COVID-19, which would help avoid severe, probably fatal, respiratory syndromes. The disclosure provides for compositions and methods of prevention and treatment of recently acquired COVID-19, i.e. the pandemic disease caused by a SARS CoV 2, which is a coronavirus.

Accordingly, in embodiments, suitable pharmaceutical formulations, and devices useful in the prevention and early treatment of COVID 19 and other diseases caused by SARS CoV 2. Are provided.

In certain embodiments, a pharmaceutical composition comprises a sulfated polysaccharide, an osmolyte(s), a buffer(s), a polyol(s) or combinations thereof. In certain embodiments, the sulfated polysaccharide is a carrageenan. In certain embodiments, the carrageenan is selected from the group consisting of iota-carrageenan, kappa-carrageenan, and lambda-carrageenan. In certain embodiments, the carrageenan is iota-carrageenan. In certain embodiments, the polyol comprises: glycerol, erythritol, mannitol, sorbitol, inositol, xylitol, threitol, maltitol or combinations thereof. In certain embodiments, the polyol is xylitol. In certain the osmolytes comprise: sodium chloride, mannitol, sorbitol or combinations thereof. In certain embodiments, the buffers comprise: citric acid/sodium citrate, disodium hydrogen phosphate/sodium dihydrogen phosphate, acetic acid/sodium acetate or combinations thereof.

In these and other embodiments, the composition comprises about 0.001 mg to about 300 mg per 100 ml of the carrageenan. In some embodiments, the composition comprises about 0.005 mg per 100 ml, about 0.075 mg per 100 ml, about 0.1 mg per 100 ml, about 0.5 mg per 100 ml, about 0.75 mg per 100 ml, about 1.0 mg per 100 ml, about 1.5 mg per 100 ml, about 2.0 mg per 100 ml, about 2.5 mg per 100 ml, about 5 mg per 100 ml, about 10 mg per 100 ml, about 12.5 mg per 100 ml, about 15 mg per 100 ml, about 20 mg per 100 ml, about 25 mg per 100 ml, about 30 mg per 100 ml, about 40 mg per 100 ml, about 50 mg per 100 ml, about 60 mg per 100 ml, about 70 mg per 100 ml, about 80 mg per 100 ml, about 90 mg per 100 ml, about 100 mg per 100 ml, about 110 mg per 100 ml, about 120 mg per 100 ml, about 130 mg per 100 ml, about 140 mg per 100 ml, about 150 mg per 100 ml, about 160 mg per 100 ml, about 170 mg per 100 ml, about 180 mg per 100 ml, about 190 mg per 100 ml, about 200 mg per 100 ml, about 210 mg per 100 ml, about 220 mg per 100 ml, about 230 mg per 100 ml, about 240 mg per 100 ml, about 250 mg per 100 ml, about 260 mg per 100 ml, about 270 mg per 100 ml, about 280 mg per 100 ml, about 290 mg per 100 ml or about 300 mg per 100 ml of the carrageenan.

In certain embodiments, a composition comprises a therapeutically effective amount of a carrageenan. In certain embodiments, a therapeutically effective amount of carrageenan is 5 µg/ml. In certain embodiments a therapeutically effective amount comprises a range from about 0.001 µg/ml to about 1 mg/ml. In certain embodiments a therapeutically effective amount of carrageenan comprises a range from about 0.005 µg/ml to about 1 mg/ml, or from about 0.01 µg/ml to about 1 mg/ml, or from about 0.015 µg/ml to about 1 mg/ml, or from about 0.020 µg/ml to about 1 mg/ml, or from about 0.025 µg/ml to about 1 mg/ml, or from about 0.03 µg/ml to about 1 mg/ml, or from about 0.04 µg/ml to about 1 mg/ml, or from about 0.05 µg/ml to about 1 mg/ml, or from about 0.06 µg/ml to about 1 mg/ml, or from about 0.07 µg/ml to about 1 mg/ml, or from about 0.080 µg/ml to about 1 mg/ml, or from about 0.09 µg/ml to about 1 mg/ml, or from about 0.1 µg/ml to about 1 mg/ml, or from about 0.5 µg/ml to about 1 mg/ml, or from about 1.0 µg/ml to about 1 mg/ml, or from about 1.5 µg/ml to about 1 mg/ml, or from about 2.0 µg/ml to about 1 mg/ml, or from about 2.5 µg/ml to about 1 mg/ml, or from about 3.0 µg/ml to about 1 mg/ml, or from about 3.5 µg/ml to about 1 mg/ml, or from about 4.0 µg/ml to about 1 mg/ml or from about 4.5 µg/ml to about 1 mg/ml, or from about 5.0 µg/ml to about 1 mg/ml.

In these and other embodiments, the composition comprises about 0.001% weight/volume (w/v) to about 20% w/v of the carrageenan based on the total of the composition. In certain embodiments, the composition comprises about 0.005% weight/volume (w/v) to about 20% w/v of the carrageenan, or from about 0.010% w/v to about 20% w/v of the carrageenan, or from about 0.015% w/v to about 20% w/v of the carrageenan, or from about 0.020% w/v to about 20% w/v of the carrageenan, or from about 0.03% w/v to about 20% w/v of the carrageenan, or from about 0.04% w/v to about 20% w/v of the carrageenan, or from about 0.05% w/v to about 20% w/v of the carrageenan, or from about 0.01% w/v to about 20% w/v of the carrageenan, or from about 0.05% w/v to about 20% w/v of the carrageenan, or from about 0.06% w/v to about 20% w/v of the carrageenan, or from about 0.07% w/v to about 20% w/v of the carrageenan, or from about 0.08% w/v to about 20% w/v of the carrageenan, or from about 0.09% w/v to about 20% w/v of the carrageenan, or from about 0.1% w/v to about 20% w/v of the carrageenan, or from about 0.2% w/v to about 20% w/v of the carrageenan, or from about 0.3% w/v to about 20% w/v of the carrageenan, or from about 0.4% w/v to about 20% w/v of the carrageenan, or from about 0.5% w/v to about 20% w/v of the carrageenan, or from about 0.6% w/v to about 20% w/v of the carrageenan, or from about 0.7% w/v to about 20% w/v of the carrageenan, or from about 0.8% w/v to about 20% w/v of the carrageenan, or from about 0.90% w/v to about 20% w/v of the carrageenan, or from about 1.00% w/v to about 20% w/v of the carrageenan, or from about 1% w/v to about 19% w/v of the carrageenan, or from about 1% w/v to about 18% w/v of the carrageenan, or from about 1% w/v to about 19% w/v of the carrageenan, or from about 1% w/v to about 18% w/v of the carrageenan, or from about 1% w/v to about 17% w/v of the carrageenan, or from about 1% w/v to about 16% w/v of the carrageenan, or from about 1% w/v to about 15% w/v of the carrageenan, or from about 1% w/v to about 14% w/v of the carrageenan, or from about 1% w/v to about 13% w/v of the carrageenan, or from about 1% w/v to about 12% w/v of the carrageenan, or from about 1% w/v to about 11% w/v of the carrageenan, or from about 1% w/v to about 10% w/v of the carrageenan based on the total of the composition.

In these and other embodiments, the composition comprises about 0.001 mg to about 30 mg per 100 ml of xylitol. In certain embodiments, the composition comprises from about 0.005 mg to about 30 mg per 100 ml of xylitol, or from about 0.01 mg to about 30 mg per 100 ml of xylitol, or from about 0.05 mg to about 30 mg per 100 ml of xylitol, or from about 0.1 mg to about 30 mg per 100 ml of xylitol, or from about 0.15 mg to about 30 mg per 100 ml of xylitol, or from about 0.2 mg to about 30 mg per 100 ml of xylitol, or from about 0.25 mg to about 30 mg per 100 ml of xylitol, or from about 0.3 mg to about 30 mg per 100 ml of xylitol, or from about 0.4 mg to about 30 mg per 100 ml of xylitol, or from about 0.5 mg to about 30 mg per 100 ml of xylitol.

In certain embodiments, the composition comprises about 0.001% weight/volume (w/v) to about 20% w/v of xylitol, or from about 0.005% w/v to about 20% w/v of xylitol, or from about 0.01% w/v to about 20% w/v of xylitol, or from about 0.02% w/v to about 20% w/v of xylitol, or from about 0.03% w/v to about 20% w/v of xylitol, or from about 0.04% w/v to about 20% w/v of xylitol, or from about 0.05% w/v to about 20% w/v of xylitol, or from about 0.06% w/v to about 20% w/v of xylitol, or from about 0.07% w/v to about 20% w/v of xylitol, or from about 0.08% w/v to about 20% w/v of xylitol, or from about 0.09% w/v to about 20% w/v of xylitol, or from about 0.1% w/v to about 20% w/v of xylitol of the total of the composition.

In these and other embodiments, the osmolyte is sodium chloride. In certain embodiments, the composition comprises from about 0.0001% weight/volume (w/v) to about 10% w/v of sodium chloride, or from about 0.0005% w/v to about 10% w/v of sodium chloride, or from about 0.001% w/v to about 10% w/v of sodium chloride, or from about 0.002% w/v to about 10% w/v of sodium chloride, or from about 0.003% w/v to about 10% w/v of sodium chloride, or from about 0.004% w/v to about 10% w/v of sodium chloride, or from about 0.005% w/v to about 10% w/v of sodium chloride, or from about 0.006% w/v to about 10% w/v of sodium chloride, or from about 0.007% w/v to about 10% w/v of sodium chloride, or from about 0.008% w/v to about 10% w/v of sodium chloride, or from about 0.009% w/v to about 10% w/v of sodium chloride, or from about 0.01% w/v to about 10% w/v of sodium chloride, or from about 0.02% w/v to about 10% w/v of sodium chloride, or from about 0.03% w/v to about 10% w/v of sodium chloride, or from about 0.04% w/v to about 10% w/v of sodium chloride, or from about 0.05% w/v to about 10% w/v of sodium chloride, or from about 0.06% w/v to about 10% w/v of sodium chloride, or from about 0.08% w/v to about 10% w/v of sodium chloride, or from about 0.08% w/v to about 10% w/v of sodium chloride, or from about 0.09% w/v to about 10% w/v of sodium chloride, or from about 0.1% w/v to about 10% w/v of sodium chloride, based on the total of the composition.

In certain embodiments, a preventive treatment to lower probability of transmission of COVID 19 or any disease caused by SARS CoV 2 comprises administrating of a therapeutically effective dose of iota carrageenan able to obtain a concentration of at least 5 µg/mL of this drug substance in the airway liquid of the lungs or nose by means of a suitable formulation and device.

In certain embodiments, a therapeutic treatment for the early stages of COVID 19 or any disease caused by SARS CoV 2 comprises the administration of a dose of iota carrageenan able to obtain a concentration of at least 5 µg/ml of this drug substance in the airway liquid of the lungs or nose.

A preventive treatment to lower probability of transmission of COVID 19 or any disease caused by SARS CoV 2 based on the administration of a dose of iota Carrageenan and xylitol able to achieve a concentration of at least 6 µg/mL of iota Carrageenan, 0.05% xylitol or a combination of at least 0.6 µg/mL of iota Carrageenan and 0.05% xylitol in the airway liquid of the lungs or nose by means of a suitable formulation and device. In certain embodiments, the dose of iota Carrageenan and xylitol able to achieve a concentration of at least 5 µg/mL of iota Carrageenan, 0.05% xylitol or a combination of at least 0.5 µg/mL of iota Carrageenan and 0.05% xylitol in the airway liquid of the lungs or nose by means of a suitable formulation and device.

In certain embodiments, a therapeutic treatment for the early stages of COVID 19 or any disease caused by SARS CoV 2 comprises administration of a therapeutically effective dose of iota carrageenan and/or xylitol able to achieve a concentration of at least 5 µg/mL of iota Carrageenan, 0.05% xylitol or a combination of at least 0.6 µg/mL of iota Carrageenan and 0.05% xylitol in the airway liquid of the lungs or nose by means of a suitable formulation and device.

In these and other embodiments, a formulation comprises about 0.01%-0.5% w/v iota carrageenan alone or 0.001-0.5% w/v iota carrageenan+0.5-10% w/v xylitol. In certain embodiments, the formulations are administered to a subject in volumes of about 50 ml up to 200 microliters of formulation per shot. In certain embodiments, one unit dose of a formulation comprising iota carrageenan alone as an active agent comprises: 5 micrograms of iota Carrageenan (0.01% in a 50 microliter unit dose) to 1000 micrograms or 1 mg of iota Carrageenan (0.5% in a 200 microliter unit dose). In certain embodiments, a unit dose of iota carrageenan+xylitol comprises: 0.5 micrograms of iota carrageenan (0.001% in a 50 microliter unit dose) to 1000 micrograms or 1 mg of iota carrageenan (0.5% in a 200 microliter unit dose).

In these and other embodiments, each unit dose is administered to each nostril. Accordingly, the total dose comprises 10 micrograms of iota carrageenan (0.01% in a 50 microliter unit dose) to 2000 micrograms or 2 mg of iota carrageenan (0.5% in a 200 microliter unit dose). With respect to a formulation comprising iota carrageenan+xylitol a total dose comprises 1 microgram of iota carrageenan (0.001% in a 50 microliter unit dose) to 2000 micrograms or 2 mg of iota carrageenan (0.5% in a 200 microliter unit dose). With respect to a composition comprising xylitol as the only active agent, the formulation comprises 500 micrograms of xylitol (0.5% in a 50 microliter unit dose) to 40 mg (5% in a 200 microliter unit dose).

In certain embodiments, a formulation comprises 250 micrograms of xylitol as the only active agent 100 µl (0.5% in a 50 microliter unit dose) to 20 mg (5% in a 200 microliter unit dose).

In certain embodiments, a nasal spray comprising a solution of iota carrageenan, osmolytes, buffers or combinations thereof. In certain embodiments, the solution comprises about 0.01% weight/volume (w/v) to about 0.50% w/v of iota carrageenan. In certain embodiments, the osmolytes comprise: sodium chloride, mannitol, sorbitol, xylitol or combinations thereof. In certain embodiments, the buffers comprise: citric acid/sodium citrate, disodium hydrogen phosphate/sodium dihydrogen phosphate, acetic acid/sodium acetate or combinations thereof. In certain embodiments, the nasal spray is delivered by a preservative-free metering pump delivering 50-200 µL of the said solution per puff.

In certain embodiments, a nasal spray comprises a solution having about 0.001% w/v to about 0.50% w/v iota carrageenan, about 0.5% w/v to about 10% w/v of xylitol. In certain embodiments, the solution comprises at least 0.001% w/v carrageenan and about 0.5% w/v to about 10% w/v of xylitol. In certain embodiments, the solution further comprises one or more of: osmolytes, buffers and combinations thereof. In certain embodiments, the osmolytes comprise at least one of: sodium chloride, mannitol, sorbitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the nasal spray is delivered by a preservative-free metering pump delivering 50-200 µL of the said solution per puff.

In certain embodiments, a nasal spray comprises a solution having about 0.01% w/v to about 0.50% w/v iota carrageenan, a preservative, osmolytes, buffers or combinations thereof. In certain embodiments, the preservative comprises: sorbic acid, potassium sorbate, benzalkonium chloride, benzoic acid, sodium benzoate, phenoxyethanol, phenyletanol or combinations thereof. In certain embodiments, the osmolytes comprise: sodium chloride, mannitol, sorbitol, xylitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the nasal spray is delivered by a preservative-free metering pump delivering 50-200 µL of the said solution per puff.

In certain embodiments, the nasal spray comprising a solution having the following composition: about 0.001% w/v to about 0.50% w/v iota carrageenan, about 0.5% w/v to about 10% w/v of xylitol. In certain embodiments, the preservative comprises: sorbic acid, potassium sorbate, benzalkonium chloride, benzoic acid, sodium benzoate, phenoxyethanol, phenyletanol or combinations thereof. In certain embodiments, the osmolytes comprise: sodium chloride, mannitol, sorbitol, xylitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the nasal spray is delivered by a preservative-free metering pump delivering 50-200 µL of the said solution per puff.

In certain embodiments, a solution for nasal or lung nebulization comprising: iota carrageenan, an osmolyte(s), a buffer(s) or combinations thereof. In certain embodiments, the osmolytes comprise: sodium chloride, mannitol, sorbitol, xylitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the solution is packaged into unit dose vials or any other suitable package for an unpreserved solution for nebulization.

In certain embodiments, a solution for nasal or lung nebulization comprising about 0.0010% w/v to about 0.50% w/v iota carrageenan and about 0.5% w/v to about 10% w/v xylitol as the active agents. In certain embodiments, the further comprising at least one osmolyte, at least one buffer or a combination thereof. In certain embodiments, the osmolytes comprise: sodium chloride, mannitol, sorbitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the solution is packaged into unit dose vials or any other suitable package for an unpreserved solution for nebulization.

In certain embodiments, a solution for nasal or lung nebulization comprises about 0.01% w/v to about 0.50% w/v iota carrageenan as the active agent, and a preservative. In certain embodiments, the preservative comprises one or more of: sorbic acid, potassium sorbate, benzalkonium chloride, benzoic acid, sodium benzoate, phenoxyethanol or phenyletanol. In certain embodiments, the solution further comprises osmolytes, buffers or a combination thereof. In certain embodiments, the osmolytes comprise at least one of: sodium chloride, mannitol, sorbitol, xylitol or combinations thereof. In certain embodiments, the buffers comprise at least one of: citric acid/sodium citrate, disodium hydrogen phosphate/sodium dihydrogen phosphate, acetic acid/sodium acetate or combinations thereof. In certain embodiments, the solution is packaged into multidose package units, comprising bottles or vials with screw caps or droppers or any other suitable multidose package for a preserved solution for nebulization.

In certain embodiments, a solution for nasal or lung nebulization comprising about 0.001% w/v to about 0.50% w/v iota carrageenan and about 0.5% w/v to about 10% w/v xylitol as the active agents, a preservative, a buffer or combinations thereof. In certain embodiments, the preservative comprises: sorbic acid, potassium sorbate, benzalkonium chloride, benzoic acid, sodium benzoate, phenoxyethanol, phenyl ethanol or combinations thereof. In certain embodiments, the e osmolytes comprise: sodium chloride, mannitol, sorbitol or combinations thereof. In certain embodiments, the buffers comprise: citric acid/sodium citrate, disodium hydrogen phosphate/sodium dihydrogen phosphate, acetic acid/sodium acetate or combinations thereof. In certain embodiments, the solution is packaged into multidose package units, comprising bottles or vials with screw caps or droppers or any other suitable multidose package for a preserved solution for nebulization.

In certain embodiments, a solution for nasal rinse or nasal wash comprising: about 0.01% w/v to about 0.50% w/v iota carrageenan as the active agent, osmolytes, buffers, preservatives or combinations thereof. In certain embodiments, the osmolytes comprise: sodium chloride, mannitol, sorbitol or combinations thereof. In certain embodiments, the buffers comprise: citric acid/sodium citrate, disodium hydrogen phosphate/sodium dihydrogen phosphate, acetic acid/sodium acetate or combinations thereof. In certain embodiments, the preservatives comprise: sorbic acid, potassium sorbate, benzalkonium chloride, benzoic acid, sodium benzoate, phenoxyethanol, phenyl ethanol or combinations thereof.

In certain embodiments, a solution for nasal or lung nebulization comprises a therapeutically effective dose of about 0.001% w/v to about 0.50% w/v iota carrageenan and about 0.5% w/v to about 10% w/v xylitol as the active agents. In certain embodiments, the solution comprises a preservative, a buffer or combinations thereof. In certain embodiments, the osmolytes comprise: sodium chloride, mannitol, sorbitol or combinations thereof. In certain embodiments, the buffers comprise: citric acid/sodium citrate, disodium hydrogen phosphate/sodium dihydrogen phosphate, acetic acid/sodium acetate or combinations thereof. In certain embodiments, the preservatives comprise: sorbic acid, potassium sorbate, benzalkonium chloride, benzoic acid, sodium benzoate, phenoxyethanol, phenyl ethanol or combinations thereof.

In certain embodiments, a nasal spray comprises: a sulfated polysaccharide as an active agent. In certain embodiments, the nasal spray comprises an osmolyte(s), a buffer(s), a polyol(s) or combinations thereof. In certain embodiments, the sulfated polysaccharide is a carrageenan. In certain embodiments, the carrageenan is selected from the group consisting of iota-carrageenan, kappa-carrageenan, and lambda-carrageenan. In certain embodiments, the carrageenan is iota-carrageenan. In certain embodiments, the nasal spray comprises about 0.001 mg to about 300 mg per 100 ml of iota-carrageenan. In certain embodiments, the polyol is xylitol. In certain embodiments, the nasal spray comprises about 0.001 mg to about 30 mg per 100 ml of xylitol. In certain embodiments, the osmolytes comprise: sodium chloride, mannitol, sorbitol or combinations thereof. In certain embodiments, the buffers comprise: citric acid/sodium citrate, disodium hydrogen phosphate/sodium dihydrogen phosphate, acetic acid/sodium acetate or combinations thereof. In certain embodiments, the nasal spray further comprises a preservative. In certain embodiments, the preservatives comprise: sorbic acid, potassium sorbate, benzalkonium chloride, benzoic acid, sodium benzoate, phenoxyethanol, phenyl ethanol or combinations thereof.

In certain embodiments, a formulation comprises 5 micrograms of iota carrageenan to 1 mg of iota carrageenan wherein a unit dose is from 50 µl up to 200 µl of the formulation. In certain embodiments, one unit dose is delivered to each nostril.

In certain embodiments, a formulation comprises about 0.001% weight/volume (w/v) to about 0.5% w/v iota carrageenan and about 0.5% w/v to about 10% w/v xylitol, wherein a unit dose is 50-200 ml of the formulation. In certain embodiments, one unit dose is delivered to each nostril.

In certain embodiments, the compositions embodied herein are administered to a patient in combination with one or more other anti-viral agents or therapeutics. Examples include any molecules that are used for the treatment of a virus and include agents which alleviate any symptoms associated with the virus, for example, anti-pyretic agents, anti-inflammatory agents, chemotherapeutic agents, and the like. In these and other embodiments, an antiviral agent in addition to such anti-viral agents of carrageenan, xylitol, includes, without limitation: antibodies, aptamers, adjuvants, anti-sense oligonucleotides, chemokines, cytokines, immune stimulating agents, immune modulating agents, B-cell modulators, T-cell modulators, NK cell modulators, antigen presenting cell modulators, enzymes, siRNA's, ribavirin, protease inhibitors, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, or combinations thereof.

In certain embodiments, a method is provided for preventing or treating a corona virus infection in a subject in need thereof by aerosolizing the pharmaceutical compositions described herein in a nasal passageway of the subject. In one embodiment, the subject is a human subject. In certain embodiments, the virus is SARS CoV 2.

In still yet another embodiment, a packaged device is provided that includes the pharmaceutical composition described herein optionally together with instructions for use. In one embodiment, the device is selected from the group consisting of aerosol dispenser, pneumatically pressurized device, multi-dose metered dose spray pump, inhaler, pump sprayer, and nebulizer.

Other aspects are discussed infra.

Definitions

The terminology used herein is for the purpose of describing particular embodiments only and is not intended to be limiting of the invention. Unless specifically defined otherwise, all technical and scientific terms used herein shall be taken to have the same meaning as commonly understood by one of ordinary skill in the art (e.g., in cell culture, molecular genetics, and biochemistry).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "active agent", refers to any molecule that is used for the prevention or treatment of a virus infection, e.g. a respiratory virus infection, and include agents which alleviate any symptom, such as runny nose, blocked nose, sore throat, sneezing, chilliness, headache, muscle ache, cough, etc., associated with the virus. Examples of active agents include carrageenan, xylitol. The "active agent" can be a compound that is directly or indirectly effective in specifically interfering with at least one viral action, such as for example, virus penetration of eukaryotic cells, virus replication in eukaryotic cells, virus assembly, virus release from infected eukaryotic cells, or that is effective in inhibiting a virus titer increase or in reducing a virus titer level in a eukaryotic or mammalian host system. It also refers to a compound that prevents from or reduces the likelihood of getting a viral infection.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "effective dose" or "effective dosage" is defined as an amount sufficient to achieve or at least partially achieve the desired effect.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used in this specification and the appended claims, the term "or" is generally employed in its sense including "and/or" unless the content clearly dictates otherwise.

The term "patient" includes human and other mammalian subjects that receive either prophylactic or therapeutic treatment.

The term "prophylactic treatment" as used herein, refers to any intervention using the compositions embodied herein, that is administered to an individual in need thereof or having an increased risk of acquiring a respiratory tract infection, wherein the intervention is carried out prior to the onset of a viral infection, e.g. SARS-CoV-2, and typically has in effect that either no viral infection occurs or no clinically relevant symptoms of a viral infection occur in a healthy individual upon subsequent exposure to an amount of infectious viral agent that would otherwise, i.e. in the absence of such a prophylactic treatment, be sufficient to cause a viral infection.

The term "therapeutically effective dose" is defined as an amount sufficient to cure or at least partially arrest the disease, e.g. COVID-19 and its complications in a patient already suffering from the disease.

The term "therapy" or "therapeutic treatment" as used herein relates to the administration of the compositions embodied herein, e.g. carrageenan, xylitol, in order to achieve a reduction in severity and/or frequency of symptoms, elimination of symptoms and/or underlying cause, prevention of the occurrence of symptoms and/or their underlying cause, and/or improvement or remediation of damage directly caused by or indirectly associated, e.g. through secondary infection, with the viral infection.

"Treatment", or "treating" as used herein, is defined as the application or administration of a therapeutic agent or combination of therapeutic agents (e.g., carrageenan and/or xylitol; optionally, another active agent, e.g. anti-viral agent preventing agent) to a patient, or application or administration of the active agent to a patient, who has a virus infection, e.g. SARS-CoV-2 with the purpose to cure, heal, alleviate, relieve, alter, remedy, ameliorate, improve or affect the infection, or symptoms thereof. The term "treatment" or "treating" is also used herein in the context of administering agents prophylactically. Accordingly, "treating" or "treatment" of a state, disorder or condition includes: (1) eradicating the virus; (2) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (3) inhibiting the state, disorder or condition, i.e., arresting, reducing or delaying the development of the disease or a relapse thereof (in case of maintenance treatment) or at least one clinical or subclinical symptom thereof; or (4) relieving the disease, i.e., causing regression of the state, disorder or condition or at least one of its clinical or subclinical symptoms. The benefit to an individual to be treated is either statistically significant or at least perceptible to the patient or to the physician.

As used herein, "a unit dose" as used herein represents the therapeutically effective amount of active ingredients, e.g. carrageenan, xylitol, that is administered to prevent or treat the viral infection. In cases where the compositions are delivered, by for example, via the nostril, each nostril will receive a unit dose.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Any compositions or methods provided herein can be combined with one or more of any of the other compositions and methods provided herein.

BRIEF DESCRIPTION OF THE DRAWINGS

In FIGS. 1-3, Vero E6 cells were treated with 600 μg/ml, 60 μg/ml, 6 μg/ml or 0.6 μg/ml pre- and post-infection with SARS-CoV-2. After a 2 h pretreatment, cells were infected with SARS-CoV-2 and incubated for 48 h in the presence of IC. Supernatants were harvested and virus yield determined by an end point dilution assay (TCID50). Controls consisted of untreated infected cells or infected cells treated with formulation without IC. Results were determined using the Reed and Muench formula and expressed as TCID50/ml. Dotted line shows the limit of detection (LOD). Testing of samples was performed in triplicate.

DETAILED DESCRIPTION

Figure 1:
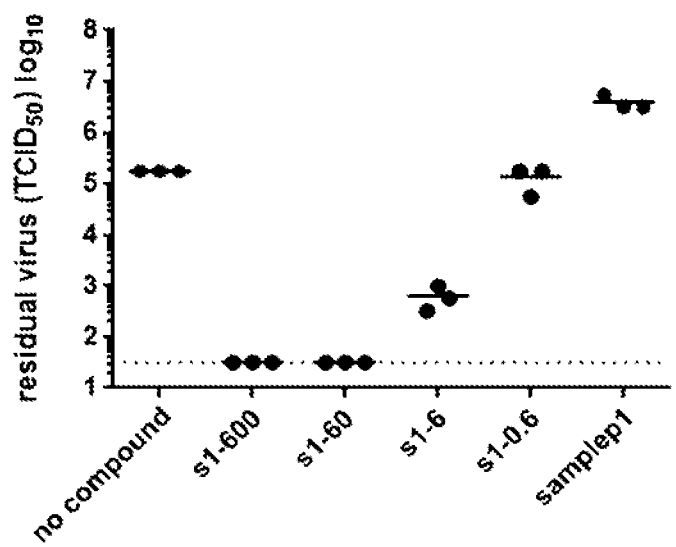
FIG. 1 is a graph demonstrating the effect of iota carrageenan on SARS-CoV-2 with Formulation #1 (1.7 mg/mL IC, 0.9% sodium chloride, 0% xylitol, pH 6-7).

The present disclosure is based, in part, on the unexpected and surprising discovery that iota Carrageenan at a concentration of not less than 6 μg/mL, a combination of iota Carrageenan and xylitol with a concentration of not less than 0.6 μg/mL of iota Carrageenan and xylitol alone are all capable of inhibiting SARS CoV 2 in vitro. These surprising results are summarized in Example 1.

Carrageenans are linear sulfated polysaccharides that are often extracted from red seaweeds. Carrageenans are commercially available in the form of kappa (κ), iota (ι) or lambda (k). Clinical trials with a formulation containing xylometazoline and iota Carrageenan revealed that the latter stays in the nasal mucosa for about 4 hrs. ((Graf et al., 2018, *International Journal of General Medicine* 2018:11 275-283), which makes it a good candidate for an antiviral nasal spray, if proved to be effective either in preventing virus cell infection and/or lowering viral load for the particular pathogen in question.

Xylitol is a polyol used as sugar substitute for diabetic patients. It is safe and have shown some antiviral properties against Influenza virus and human respiratory syncytial virus when ingested (Xu et al., *Biol. Pharm. Bull.* 39, 540-546 (2016); Yin S. Y. et al. (2014) *PLoS ONE* 9(1): e84633. doi: 10.1371/journal.pone.0084633). Xylitol is used as an osmolyte in nasal sprays, as well.

Both iota carrageenan and xylitol are safe for humans, being used in much larger amounts as food additive and sweetener, respectively, than those that may be used for nasal delivery. Nasal safety of iota Carrageenan by nasal and nebulization administration has been already confirmed empirically (Hebar A. et al. (2015), PLoS ONE 10(4): e0122911. doi: 10.1371/journal.pone.0122911). The same holds for 5% Xylitol water solution both applied as nasal spray and nasal irrigation (Weissman J. D. et al., *Laryngoscope*, 121:2468-2472, 2011), as well as applied as a nebulization solution (Durairaj L. et al., 2004, *Respiratory Research* 2004, 5:13 doi:10.1186/1465-9921-5-13).

In another embodiment, a solution comprises: iota carrageenan from about 0.01 to about 0.5% w/v, iota Carrageenan from about 0.001 to 0.5% w/v and xylitol in a 0.5-10% w/v or xylitol in a concentration from 0.5 to 10% w/v. An osmolyte may be added from the group: sodium chloride, mannitol, sorbitol, glycerin or any other well known in the art. The said formulation is packaged into a nasal spray to be delivered to the nose as one puff of 50-200 μL into each nostril each 4 hours during waking hours. The solution may contain suitable buffers, such citric acid/sodium citrate, disodium phosphate, dihydrogen sodium phosphate, acetic acid/sodium acetate or other buffers known in the art. This formulation is based on the surprising result of Example 1 and the following estimations: iota carrageenan has a residence time of approximately 4 hour; taking into account that surface area of the nasal mucosa is 100-250 $cm^2$ (Bitter C et al. (2011), *Curr Probl Dermatol. Basel*, Karger, 2011, vol 40, pp 20-35, Garcia G J M et al. (2008), *Inhalation Toxicology*, 2009; 21(7): 607-618, DOI: 10.1080/08958370802320186, Gizurarzon S (2012), *Current Drug Delivery*, 2012, 9, 566-582, Pires A et al. (2009), *J Pharm Pharmaceut Sci* 12(3) 288-311, 2009) and that the airway surface liquid height, though variable, would be 5-15 μm (Helassa N et al. (2014), *Biochem. J.*, (2014) 464, 213-220, doi:10.1042/BJ20141041, Wagenman et al. (1992), *J Allergy Clin Immunol, Vol.* 90, No. 3, Part 2, pp 419-423), the airway surface liquid volume is within 50 and 375 μL.

Accordingly, administering a 0.01% w/v of iota carrageenan and 5% xylitol in 1 puff of 100 μl per nostril, provides a nasal concentration of iota carrageenan of at least 35 μg/mL and 1.74% w/v xylitol used as an osmolyte enhances further the antiviral action in vivo by lowering the ionic strength of the nasal airway surface liquid and thus improving the innate antiviral action of defensins (Klotman M E et al., 2006, Nature Reviews/Immunology, Vol. 6, June 2006, pp 447-456, Furci L et al. 2012, *PLoS ONE* 7(9): e45208. doi: 10.1371/journal.pone.0045208,).

The nasal formulation may be sterilized by filtration as taught by (Grassauer 2016, CA 2992352 A1) and filled aseptically into suitable bottles, snapping appropriate preservative free nasal pumps onto them. Possible realizations of this embodiment are described in Examples 2, 3, 4 and 5.

In another embodiment, a solution comprises: iota carrageenan from about 0.01 to about 0.5% w/v, iota Carrageenan from about 0.001 to 0.5% w/v and xylitol in a 0.5-10% w/v or xylitol in a concentration from 0.5 to 10% w/v. An osmolyte may be added from the group: sodium chloride, mannitol, sorbitol, glycerin or any other well known in the art. This solution also contains sorbic acid, potassium sorbate, parabens, benzalkonium chloride, benzoic acid, sodium benzoate, phenoxyethanol, phenyl ethanol or other suitable preservatives known in the art with or without the addition of chelating agents, such as citric acids, sodium citrate or sodium salts of edetic acid may be added to the formulation to preserve it, allowing a non-sterile nasal formulation in bottles fitted with standard nasal pumps as taught in Examples 6, 7 and 8.

In another embodiment a solution for either nasal or lung nebulization solution comprises: iota carrageenan from about 0.01 to about 0.5% w/v, iota Carrageenan from about 0.001 to 0.5% w/v and xylitol in a 0.5-10% w/v or xylitol in a concentration from 0.5 to 10% w/v. In certain embodiments, the solution further comprises sodium chloride or another suitable osmolyte such as mannitol, sorbitol, and others well known in the art is packaged into unpreserved unit dose vials to be used for the nebulization of patients. The solution may contain suitable buffers, such citric acid/ sodium citrate, disodium phosphate, dihydrogen sodium phosphate or other buffers known in the art. In this pharmaceutical form higher volumes are usually employed and, therefore, even lower concentrations of iota carrageenan allow the administration of suitable mass doses of this drug substance. At the same time, nasal nebulization reaches a more extensive area of the nasal cavity, particularly the deeper and higher portions (Moffa 2019). The nasal nebulization is particularly useful in treating patients in early stages of a respiratory disease caused by SARS CoV 2, such as pandemic COVID 19. Lung nebulization is helpful for patients and may be practiced by using the same composition in a nebulizer. This embodiment is illustrated in examples 9, 10 and 11.

In still another embodiment, a solution for either nasal or lung nebulization solution comprises: iota carrageenan from about 0.01 to about 0.5% w/v, iota Carrageenan from about 0.001 to 0.5% w/v and xylitol in a 0.5-10% w/v or xylitol in a concentration from 0.5 to 10% w/v with the possible addition of sodium chloride or another suitable osmolyte such as mannitol, sorbitol, and others well known in the art. This solution also contains sorbic acid, potassium sorbate, parabens, benzalkonium chloride, benzoic acid, sodium benzoate, phenoxyethanol, phenyl ethanol or other suitable preservatives known in the art with or without the addition of chelating agents, such as citric acids, sodium citrate or sodium salts of edetic acid may be added to the formulation to preserve it. This solution is packaged into multidose vials to be used for the nasal and/or lung nebulization of patients at early stages of the disease. This embodiment is illustrated in examples 12 and 13.

In another embodiment, a solution for nasal lavage or nasal wash comprises: iota carrageenan from about 0.01 to about 0.5% w/v, iota Carrageenan from about 0.001 to 0.5% w/v and xylitol in a 0.5-10% w/v or xylitol in a concentration from 0.5 to 10% w/v. with the possible addition of sodium chloride or another suitable osmolyte such as mannitol, sorbitol, and others well known in the art is packaged into either spray bottles or aerosol cans fitted with continuous valves. The formulation may contain sorbic acid, potassium sorbate, parabens, benzalkonium chloride, benzoic acid, sodium benzoate, phenoxyethanol, phenyl ethanol or other suitable preservatives known in the art with or without the addition of chelating agents, such as citric acids, sodium citrate or sodium salts of edetic acid, allowing for a preserved non-sterile nasal wash formulation. This practical device helps rinse the nose with these active ingredients and may eliminate more thoroughly viruses present in the whole of the nasal cavity. They are particularly suitable for the early stages of SARS CoV 2 infection. This embodiment is illustrated in examples 14 and 15.

Accordingly, the compositions referred to herein comprising iota and/or kappa carrageenan is also active against coronaviruses, e.g. COVID-19, including other respiratory viruses such as, human rhinovirus, a member of the paramyxoviridae such as parainfluenza virus, metapneumovirus, or respiratory syncytial virus, a member of the orthomyxoviridae such as influenza virus, or an adenovirus subtype B(ICD-10 codes J09 and J10).

The composition can include a pharmaceutically acceptable carrier, e.g., one or more solvents, dispersion media, coatings, antimicrobial agents, isotonic and absorption delaying agents, and the like, compatible with administration to a mammal, such as a human. Any carrier compatible with the excipient(s) and therapeutic agent(s) is suitable for use. Supplementary active compounds may also be incorporated into the compositions.

In certain embodiments, the pharmaceutical compositions are specifically adapted for topical administration to the nasal cavity. The pharmaceutical compositions may be applied before or after the outbreak of a respiratory viral infection in a human individual. Even if applied after the outbreak of a viral infection the compositions still prevent or at least ameliorate late complications of respiratory viral infections. Such complications are known in the art and include—but are not limited to—complications in connection with secondary infections by bacteria, and deterioration of pre-existing diseases such as allergy or COPD.

Topically administrable intranasal compositions referred to herein may have a pH value within a range of from 3.5 to 8.0, usually within a range of from about 4.0 to about 8.0. They may comprise one or more nasally compatible pH adjusting agents or buffer systems that prevent pH drift during storage. Such pH adjusting agents include, but are not limited to, boric acid, sodium borate, potassium citrate, citric acid, sodium bicarbonate, and various inorganic phosphate buffers such as $Na_2HPO_4$, $NaH_2PO_4$, $KH_2PO_4$, and mixtures thereof. The minimal ionic strengths introduced by any such pH-adjusting agents do not interfere with the essence of the invention. To prevent precipitation of calcium with phosphate ions from the buffer system, EDTA may be added up to a concentration of 2 mg/ml. In addition, flavors such as *eucalyptus*, campher, menthol, peppermint or similar, by way of oils or extracts, may be added to the product at concentrations known in the art.

Also, the topical intranasal formulations referred to herein may comprise one or more intranasally compatible surfactants. The surfactant facilitates the spread of the formulation across the surface of the nasal mucosa and may be non-ionic or anionic. Exemplary non-ionic surfactants may be selected from the group comprising tyloxapol, polyoxyethylene sorbitan esters, polyethoxylated castor oils, poloxamers, polyoxyethylene/polyoxypropylene surfactants, polyoxyethylene stearate, polyoxyethylene propylene glycol stearate, hydroxyalkylphosphonate,lauric or palmitic acid esters and ethers, triethanol amine oleate, or from a combination of the foregoing agents. Still further suitable surfactants may be known to those skilled in the art. The surfactants may typically be present at concentrations of from 0.02% (w/v) to 0.1% (w/v) of the composition.

In various embodiments, the present topical intranasal preparation may contain one or more preservatives to inhibit microbial growth and to prolong shelf life. Exemplary preservatives include, but are not limited to, disodium edetate (EDTA) and potassium sorbate. The preservative amount is typically less than about 0.02% (w/v) of the total composition, EDTA may be added up to 2 mg/ml.

In addition to the ingredients mentioned above, it is contemplated that a variety of additional or alternative ingredients may be present in the pharmaceutical compositions of the present disclosure, which additional or alternative ingredients include anti-oxidants such as vitamin E or its commercially available derivatives such as tocopherol polyethylene glycol 1000 succinate (TPGS), ascorbic acid, or sodium metabisulfite.

The pharmaceutical compositions herein are typically provided in sterile form for topical administration to the nasal cavity and are preferably adjusted for self-administration by the individual in need thereof. In one embodiment, the preparation is a particle-free nasal spray. Other suitable formulations include intranasally acceptable swabs, as well as ointments and gels that can be applied to the nose, optionally as sprays or aerosols.

Pharmaceutical compositions described above can be delivered via different methodologies including sprays, irrigation systems (e.g. netipot), syringes or others. The composition may be provided in a dosage form that is suitable for a nasal aerosol or inhalation administration route. An exemplary method of administration of the composition can include spraying vaporized or nebulized disseminated microparticles under an active dynamic pressure.

Suitable aerosol dispensers for use will be apparent to those skilled in the art and may vary from simple devices analogous to perfume dispensers to pressurized spray cans and even complex apparatus such as might be used in hospitals. Whichever device is used it is generally preferable that it comprises some kind of dosimeter to control the amount of solution administered in one go. One device, which corresponds to a dispenser with a nozzle, effectively incorporates such a dosimeter without any specialized adaptation being necessary, the limit stop of the depressible spray head fixing the maximum single amount of solution dispensable at once. Specially developed spray devices may be made with a hand-held device comprising a reservoir of the composition.

Suitable means for dispersing the spray, preferably in aerosol form, are provided. Examples include pneumatically pressurized devices and devices employing pressurized gas forced across the opening of a tube leading into the reservoir to create an aerosol, and press-button type devices wherein the button, when pressed, creates pressure on the surface of the liquid in the reservoir, forcing it up through a tube and through a fine nozzle to disperse the solution into an aerosol spray. Other examples include aerosol dispensers, inhalers, pump sprayers, nebulizers (such as positive pressure nebulizers), and the like. In some embodiments, the device used is pre-filled with a composition described herein.

One embodiment would include a multi-dose metered dose spray pump allowing for spraying of a fixed volume of solution. Alternatively, gas driven (e.g. nitrogen) devices, such as systems that hold the compositions separate from the propellant in aluminum or plastic (or any other type of) bottle. These devices deliver solution at variable diffusion flows and angles when combined with different actuators. Preferred diffusion flows could deliver 0.5-10 ml solution per spraying second at angles of 0-60°.

The compositions described above can be administered as per physician's instructions and depending on the condition. A preferred mode of (nasal) administration comprises 1-5 sprays per nostril, 1-5 times daily; this could extend to many weeks depending on the condition or symptom to be treated (e.g. in allergy).

The therapeutic methods described herein (that include prophylactic treatment) in general comprise administration of a therapeutically effective amount of the compositions herein to a subject (e.g., animal, human) in need thereof, including a mammal, particularly a human. Such treatment will be suitably administered to subjects, particularly humans, suffering from, having, susceptible to, or at risk for infection by respiratory tract viruses or symptoms thereof. Determination of those subjects "at risk" can be made by any objective or subjective determination by a diagnostic test or opinion of a subject or health care provider.

EXAMPLES

Examples are provided below to facilitate a more complete understanding of the invention. The following examples illustrate the exemplary modes of making and practicing the invention.

Example 1 In Vitro Inhibition of SARS-CoV-2 Using Iota Carrageenan

The aim of this study was to determine if Iota Carrageenan demonstrates antiviral activity against SARS-CoV-2.

An in vitro experiment performed under controlled conditions have demonstrated that even at concentrations of 6 µg/mL iota Carrageenan alone is capable of significantly reducing viral titers of SARS CoV 2 in Vero cell cultures in vitro. A combination of 5% xylitol and iota Carrageenan reduces by at least 5000 times the virus titer in Vero cell cultures in vitro, even using concentrations of iota Carrageenan as low as 0.6 µg/mL. Moreover, 5% xylitol alone reduces by at least 5000 times virus titer in Vero cell cultures in vitro.

The following table summarizes the formulations tested for antiviral capacity against SARS CoV 2:

| Component | Sample 1 | Sample 2 | Sample 3 |
|---|---|---|---|
| Iota Carrageenan | 1.7 mg/ml | 1.2 mg/ml | 1.2 mg/ml |
| Sodium Chloride (NaCl) | 0.9% | 0.5% | 0% |
| Xylitol | 0% | 0% | 5% |
| pH adjusted to | 6.00-7.00 | 6.00-7.00 | 6.00-7.00 |
| Sodium Chloride (NaOH) | 0.9% | 0.5% | 0% |
| Xylitol | 0% | 0% | 5% |
| pH adjusted to | 6.00-7.00 | 6.00-7.00 | 6.0-7.00 |

The data obtained are summarized below

TABLE 1

| Log reduction of TCID50/mL after 48 hs. (mean of three replicates) | | | |
|---|---|---|---|
| Iota Carrageenan | Sample 1 | Sample 2 | Sample 3 |
| 600 µg/mL | ≥3.75 | ≥4.25 | ≥4.25 |
| 60 µg/mL | ≥3.75 | ≥4.25 | ≥4.25 |
| 6 µg/mL | 2.45 | >4.25 | >4.25 |
| 0.6 µg/mL | 0.1 | 0.65 | >4.25 |

Samples P1, P2 and P3 did not contain iota Carrageenan

| Iota Carrageenan | Sample P1 | Sample P2 | Sample P3 |
|---|---|---|---|
| 0 ng/mL | None | None | >4.25 |

All data are surprising. However, the antiviral activity of xylitol on its own as shown in the viral titer reduction of Sample P3 is particularly remarkable.

A detailed description of the test protocols and results follows:

Materials:
Vero E6
T-175 tissue culture flask
0.25% Trypsin-EDTA (1×)
Minimum Essential Medium (MEM) with Earle's salts and L-glutamine, VWR Cat #10-010-CV
Dulbecco's Phosphate Buffered Saline 1×
Fetal bovine serum (FBS), BioWest Cat #S1620, Heat inactivated, (Lot No: 055G17)

Greiner Bio-one TC treated PS sterile cell culture 12 well plates (Cat #07-000-691)

Virus: SARS-CoV-2 UTHSC passage 2, (SARS-Related Coronavirus 2 Isolate USA-WA1/2020)

Samples:
  Sample 1: 600 mcg/mL; 60 mcg/mL, 6 mcg/mL and 0.6 mcg/mL
    To obtain the highest concentration a dilution of 7 mL of Sample 1+3 mL of Sample P1 (or bringing to 10 mL with Sample P1) was used.
    The stock solution having a concentration of 1200 mcg/mL may be used to obtain the highest final concentration (600 mcg/mL) by applying 0.5 mL in each of the wells tested.
    The rest of 1/10 dilutions were obtained using Sample P1 as diluting agent.
    All concentrations and control were tested in triplicate.
  Sample 2: 600 mcg/mL; 60 mcg/mL, 6 mcg/mL and 0.6 mcg/mL.
    To obtain the highest concentration 0.5 mL of Sample 2 was directly applied in each well.
    To obtain the 1/10 dilutions, use Sample P2 as diluting agent.
    All concentrations tested in triplicate.
  Sample 3: 600 mcg/mL; 60 mcg/mL, 6 mcg/mL and 0.6 mcg/mL.
    To obtain the highest concentration directly apply 0.5 mL of Sample 3 in each well.
    To obtain the 1/10 dilutions, use Sample P3 as diluting agent.
    All concentrations tested in triplicate.

Methodology:
1) Seed $2.5 \times 10^5$ Vero E6 cells to each well in 12-well plate.
2) Allow cells to grow overnight. No swirling, otherwise cell density will be lower in the center of the well. Cells should be 70-90% confluent the day of infection.
3) Next day remove media, wash each well once with 1 ml PBS
4) Add:
  a) 0.5 ml fresh media (MEM+2% FBS+1% P-S)+0.5 ml Sample 1, 2, or 3 (final concentrations in 1 ml total: 600 mcg/mL; 60 mcg/mL, 6 mcg/mL and 0.6 mcg/mL) b) 0.5 ml fresh media+0.5 ml Sample P1, P2, or P3 equivalent (Sample equivalent volume amount in µl)
5) Include virus only and cells only control on the plates
6) Incubate for 2 hr at 37° C. and then remove well components
7) Add SARS-CoV-2, $5 \times 10^4 / 0.2$ ml (MOI=0.1) diluted in MEM+2% FBS, to each well.
8) Incubate for 1 hr at 37° C. Swirl the plates every 15 min
9) After 1 hr, remove virus, add:
  a) 0.5 ml fresh media (MEM+2% FBS+1% P-S)+0.5 ml Sample 1, 2, or 3 (final concentrations in 1 ml total: 600 mcg/mL; 60 mcg/mL, 6 mcg/mL and 0.6 mcg/mL)
  b) 0.5 ml fresh media+0.5 ml Sample P1, P2, or P3 equivalent (Sample equivalent volume amount in µµl)
10) Incubate for 2 days at 37° C.
11) After 2 days, harvest components from each well and perform TCID50 assay $TCID_{50}$ Assay:

Residual virus was measured by TCID50 assay in 96-well plate format with 3 wells per dilution of virus. 10-fold serial dilutions ($10^{-1}$ to $10^{-7}$) of collected samples (treated, control, or virus only) were used to infect Vero E6 cells in a 96-well plate. The cell plates were incubated at 37° C., 5% CO2, with humidity for an additional 2 days. After 2 days, Cell Titer Glo was used to determine viability of cells. The virus endpoint titer was determined using the Reed-Muench formula and expressed as log TCID50/mL.

TABLE 1

| | | TCID50/mL Data | | | | |
|---|---|---|---|---|---|---|
| | | TCID50/ml Replicates | | | | |
| | | 1 | 2 | 3 | Mean | Log Reduction |
| | Virus Only | 1.78E+05 | 1.78E+05 | 1.78E+05 | 1.78E+05 | | |
| Formulation #1 | 600 ug/ml | 3.16E+01 | 3.16E+01 | 3.16E+01 | 3.16E+01 | 3.75 | LOD |
| | 60 ug/ml | 3.16E+01 | 3.16E+01 | 3.16E+01 | 3.16E+01 | 3.75 | LOD |
| | 6 ug/ml | 5.62E+02 | 3.16E+02 | 1.00E+03 | 6.26E+02 | 2.453294082 | |
| | 0.6 ug/ml | 1.78E+05 | 5.62E+04 | 1.78E+05 | 1.37E+05 | 0.112339991 | |
| P1 Control | 0 ug/ml | 3.16E+06 | 5.62E+06 | 3.16E+06 | 3.98E+06 | | |

TABLE 2

| | | TCID50/mL Data | | | | |
|---|---|---|---|---|---|---|
| | | TCID50/ml Replicates | | | | |
| | | 1 | 2 | 3 | Mean | Log Reduction |
| | Virus Only | 5.62E+05 | 5.62E+05 | 5.62E+05 | 5.62E+05 | | |
| Formulation #2 | 600 ug/ml | 3.16E+01 | 3.16E+01 | 3.16E+01 | 3.16E+01 | 4.25 | LOD |
| | 60 ug/ml | 3.16E+01 | 3.16E+01 | 3.16E+01 | 3.16E+01 | 4.25 | LOD |
| | 6 ug/ml | 3.16E+01 | 3.16E+01 | 3.16E+01 | 3.16E+01 | 4.25 | LOD |
| | 0.6 ug/ml | 3.16E+05 | 3.16E+04 | 3.16E+04 | 1.26E+05 | 0.647940009 | |
| P2 Control | 0 ug/ml | 5.62E+05 | 3.16E+05 | 5.62E+05 | 4.80E+05 | | |

TABLE 3

TCID50/mL Data

|  |  | \multicolumn{3}{c}{TCID50/ml Replicates} | | | |
| --- | --- | --- | --- | --- | --- | --- |
|  |  | 1 | 2 | 3 | Mean | Log Reduction |
|  | Virus Only | 5.62E+05 | 5.62E+05 | 5.62E+05 | 5.62E+05 |  |
| Formulation #3 | 600 ug/ml | 3.16E+01 | 3.16E+01 | 3.16E+01 | 3.16E+01 | 4.25 LOD |
|  | 60 ug/ml | 3.16E+01 | 3.16E+01 | 3.16E+01 | 3.16E+01 | 4.25 LOD |
|  | 6 ug/ml | 3.16E+01 | 3.16E+01 | 3.16E+01 | 3.16E+01 | 4.25 LOD |
|  | 0.6 ug/ml | 3.16E+01 | 3.16E+01 | 3.16E+01 | 3.16E+01 | 4.25 LOD |
| P3 Control | 0 ug/ml | 3.16E+01 | 3.16E+01 | 3.16E+01 | 3.16E+01 | 4.25 LOD |

Figure 2:
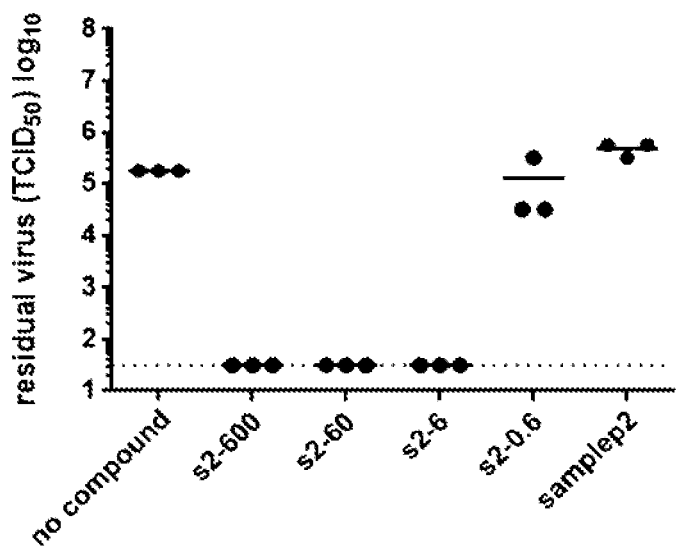
FIG. 2 is a graph demonstrating the effect of iota carrageenan on SARS-CoV-2 Formulation #2 (1.2 mg/mL IC, 0.5% sodium chloride, 0% xylitol, pH 6-7).
Figure 3:
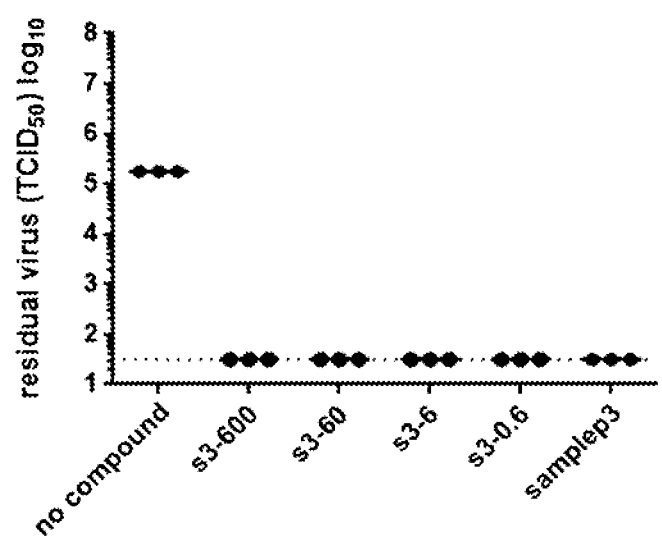
FIG. 3 is a graph demonstrating the effect of iota carrageenan on SARS-CoV-2 Formulation #3 (1.2 mg/mL IC, 0% sodium chloride, 0.5% xylitol, pH 6-7).

Effect of Iota Carrageenan on SARS-CoV-2 is shown in FIGS. 1-3. Vero E6 cells were treated with 600 μg/ml, 60 μg/ml, 6 μg/ml or 0.6 μg/ml pre- and post-infection with SARS-CoV-2. After a 2 h pretreatment, cells were infected with SARS-CoV-2 and incubated for 48 h in the presence of IC. Supernatants were harvested and virus yield determined by an end point dilution assay (TCID50). Controls consisted of untreated infected cells or infected cells treated with formulation without IC. Results were determined using the Reed and Muench formula and expressed as TCID50/ml. Dotted line shows the limit of detection (LOD). Testing of samples was performed in triplicate.

Results:

To examine the antiviral effects of Iota Carrageenan (IC) on SARS-CoV-2, three formulations were developed and tested. Each of the three formulations were tested in a dose dependent manner and ranged from 600 μg/ml to 0.6 μg/ml. The composition of each formulation was as follows:

Formulation #1: SARS-CoV-2 samples treated with 600 μg/ml and 60 μg/ml of IC were reduced ≥3.75 Log when compared to untreated control. The 6 μg/ml concentration of IC also demonstrated an effect but to a lesser extent, with a 2.5 Log reduction in virus. At 0.6 μg/ml, IC did not demonstrate activity and was comparable to the untreated control. Lastly, there was no reduction in virus with P1, providing evidence that IC and not the components of formulation #1 is inhibiting SARS-CoV-2.

Formulation #2: SARS-CoV-2 samples treated with 600 μg/ml, 60 μg/ml, and 6 μg/ml of IC were reduced ≥4.25 Log when compared to untreated control. At 0.6 μg/ml, IC did not demonstrate activity and was comparable to the untreated control. No reduction in virus with P2 was observed, providing evidence that IC and not the components of formulation #2 is inhibiting SARS-CoV-2.

Formulation #3: All concentrations demonstrated antiviral activity including the P3 control. Xylitol was present in this formulation and suggests this component might also exert an antiviral effect.

Example 2

A nasal spray pharmaceutical formulation comprising:

| Component | Amount per 100 mL | Function |
| --- | --- | --- |
| Iota Carrageenan | 120 mg | Active Ingredient |
| NaCl | 0.50 g | Active ingredient |
| HCl/NaOH | s.q. pH 5-7.5 | pH adjustment agents |
| Water | s.q. 100 mL | Vehicle |

This formulation was manufactured in the following way to manufacture 100 L of bulk solution, yielding ca. 8,800 10-mL nasal sprays (an overfill is needed to obtain 10 mL extractable volume):

1. Iota carrageenan (120 g) is dissolved in 90 Liter of Purified Water under stirring in a mixing tank.
2. NaCl (0.50 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into bottles
7. Preservative-free metered nasal pumps are snapped onto the bottle necks
8. Units are labeled and packaged for distribution In this preparation Purified Water may be replaced by Water for Injection.

Example 3

A nasal spray pharmaceutical formulation comprising:

| Component | Amount per 100 mL | Function |
| --- | --- | --- |
| Iota Carrageenan | 170 mg | Active Ingredient |
| NaCl | 0.90 g | Active ingredient |
| HCl/NaOH | s.q. pH 5-7.5 | pH adjustment agents |
| Water | s.q. 100 mL | Vehicle |

This formulation was manufactured in the following way to manufacture 100 L of bulk solution, yielding ca. 8,800 10-mL nasal sprays (an overfill is needed to obtain 10 mL extractable volume):

1. Iota carrageenan (170 g) is dissolved in 90 Liter of Purified Water under stirring in a mixing tank.
2. NaCl (0.90 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into bottles
7. Preservative-free metered nasal pumps are snapped onto the bottle necks
8. Units are labeled and packaged for distribution In this preparation Purified Water may be replaced by Water for Injection.

Example 4

A nasal spray pharmaceutical formulation comprising:

| Component | Amount per 100 mL | Function |
| --- | --- | --- |
| Iota Carrageenan | 120 mg | Active Ingredient |
| Xylitol | 7.00 g | Active ingredient |
| HCl/NaOH | s.q. pH 5-7.5 | pH adjustment agents |
| Water | s.q. 100 mL | Vehicle |

This formulation was manufactured in the following way to manufacture 100 L of bulk solution, yielding ca. 8,800 10-mL nasal sprays (an overfill is needed to obtain 10 mL extractable volume):

1. Iota carrageenan (120 g) is dissolved in 90 Liter of Purified Water under stirring in a mixing tank.
2. Xylitol (7 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into bottles
7. Preservative-free metered nasal pumps are snapped onto the bottle necks
8. Units are labeled and packaged for distribution In this preparation Purified Water may be replaced by Water for Injection.

Example 5

A nasal spray pharmaceutical formulation comprising:

| Component | Amount per 100 mL | Function |
| --- | --- | --- |
| Xylitol | 0.50 g | Active ingredient |
| NaCl | 0.81 g | Osmolyte |
| HCl/ NaOH | s.q. pH 5-7.5 | pH adjustment agents |
| Water | s.q. 100 mL | Vehicle |

This formulation was manufactured in the following way to manufacture 100 L of bulk solution, yielding ca. 8,800 10-mL nasal sprays (an overfill is needed to obtain 10 mL extractable volume):

1. Xylitol (0.5 kg) is added and dissolved under stirring
2. NaCl (0.81 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into bottles
7. Preservative-free nasal metered pumps are crimped onto the bottle necks
8. Units are labeled and packaged for distribution In this preparation Purified Water may be replaced by Water for Injection.

Example 6

A nasal spray pharmaceutical formulation comprising:

| Component | Amount per 100 mL | Function |
| --- | --- | --- |
| Iota Carrageenan | 170 mg | Active Ingredient |
| NaCl | 0.90 g | Active ingredient |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

A pharmaceutical formulation was manufactured in the following way to manufacture 100 L of bulk solution, yielding ca. 8,800 10-mL nasal sprays (an overfill is needed to obtain 10 mL extractable volume):

1. Iota carrageenan (170 g) is dissolved in 90 Liter of Purified Water under stirring in a mixing tank.
2. NaCl (0.9 kg) is added and dissolved under stirring
3. Potassium Sorbate (0.20 kg) is added and dissolved under stirring
4. Disodium Edetate (0.10 kg) is added and dissolved under stirring.
5. Either HCl or NaOH is added to reach pH between 6 and 7.5
6. The solution is brought to volume with additional Purified Water
7. The final solution is filled into bottles.
8. Metered nasal pumps are snapped onto the bottle necks
9. Units are labeled and packaged for distribution

Example 7

A nasal spray pharmaceutical formulation comprising:

| Component | Amount per 100 mL | Function |
| --- | --- | --- |
| Iota Carrageenan | 120 mg | Active Ingredient |
| Xylitol | 5.00 g | Active ingredient |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

A pharmaceutical formulation was manufactured in the following way to manufacture 100 L of bulk solution, yielding ca. 8,800 10-mL nasal sprays (an overfill is needed to obtain 10 mL extractable volume):

1. Iota Carrageenan (120 g) is dissolved in 90 Liter of Purified Water under stirring in a mixing tank.
2. Xylitol (5 kg) is added and dissolved under stirring
3. Potassium Sorbate (0.20 kg) is added and dissolved under stirring
4. Disodium Edetate (0.10 kg) is added and dissolved under stirring.
5. Either HCl or NaOH is added to reach pH between 6 and 7.5
6. The solution is brought to volume with additional Purified Water
7. The final solution is filled into bottles.
8. Metered nasal pumps are crimped onto the multidose bottles
9. Units are labeled and packaged for distribution

Example 8

A nasal spray pharmaceutical formulation comprising:

| Component | Amount per 100 mL | Function |
|---|---|---|
| Iota Carrageenan | 170 mg | Active Ingredient |
| Xylitol | 0.50 g | Active ingredient |
| NaCl | 0.81 g | Osmolyte |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

A pharmaceutical formulation was manufactured in the following way to manufacture 100 L of bulk solution, yielding ca. 8,800 10-mL nasal sprays (an overfill is needed to obtain 10 mL extractable volume):

1. Iota Carrageenan (170 g) is dissolved in 90 Liter of Purified Water under stirring in a mixing tank.
2. Xylitol (5 kg) is added and dissolved under stirring
3. Potassium Sorbate (0.20 kg) is added and dissolved under stirring
4. Disodium Edetate (0.10 kg) is added and dissolved under stirring.
5. Either HCl or NaOH is added to reach pH between 6 and 7.5
6. The solution is brought to volume with additional Purified Water
7. The final solution is filled into bottles.
8. Metered nasal pumps are snapped onto the bottles
9. Units are labeled and packaged for distribution

Example 9

A pharmaceutical formulation for either nasal or lung nebulization comprising:

| Component | Amount per 100 mL | Function |
|---|---|---|
| Iota Carrageenan | 50.0 mg | Active Ingredient |
| NaCl | 0.90 g | Active ingredient |
| HCl/NaOH | s.q. pH 5-7.5 | pH adjustment agents |
| Water | s.q. 100 mL | Vehicle |

This formulation contains 1 mg each 2 ml to be nebulized into both nostrils or into the lungs in a dose similar to the nasal sprays. NaCl is formulated at 0.90%.

This formulation was manufactured in the following way to manufacture 100 L of bulk solution, yielding ca 47,600 2-mL unit dose vials (an overfill is needed to obtain 3 mL extractable volume):

1. Iota Carrageenan (50 g) is dissolved in 90 Liter of Purified Water under stirring in a mixing tank.
2. NaCl (0.90 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into unit dose vials.
7. Vials are packaged for distribution In this preparation Purified Water may be replaced by Water for Injection.

Example 10

A pharmaceutical formulation for either nasal or lung nebulization comprising:

| Component | Amount per 100 mL | Function |
|---|---|---|
| Iota Carrageenan | 100.0 mg | Active Ingredient |
| Xylitol | 5.00 g | Active ingredient |
| HCl/NaOH | s.q. pH 5-7.5 | pH adjustment agents |
| Water | s.q. 100 mL | Vehicle |

This formulation contains 2 mg each 2 ml to be nebulized into both nostrils or into the lungs in a dose similar to the nasal sprays. Xylitol is formulated at 5%.

This formulation was manufactured in the following way to manufacture 100 L of bulk solution, yielding ca 47,600 2-mL unit dose vials (an overfill is needed to obtain 3 mL extractable volume):

1. Iota Carrageenan (100 g) is dissolved in 90 Liter of Purified Water under stirring in a mixing tank.
2. Xylitol (5 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into unit dose vials.
7. Vials are packaged for distribution In this preparation Purified Water may be replaced by Water for Injection.

Example 11

A pharmaceutical formulation for either nasal or lung nebulization comprising:

| Component | Amount per 100 mL | Function |
|---|---|---|
| Iota Carrageenan | 50.0 mg | Active Ingredient |
| Xylitol | 0.50 g | Active ingredient |
| NaCl | 0.81 g | Osmolyte |
| HCl/NaOH | s.q. pH 5-7.5 | pH adjustment agents |
| Water | s.q. 100 mL | Vehicle |

This formulation contains 1 mg each 2 ml to be nebulized into both nostrils or into the lungs in a dose similar to the nasal sprays. Xylitol and NaCl are formulated at 0.50% and 0.81% w/v.

This formulation was manufactured in the following way to manufacture 100 L of bulk solution, yielding ca 47.600 2-mL unit dose vials (an overfill is needed to obtain 3 mL extractable volume):

1. Iota Carrageenan (50.0 g) is dissolved in 90 Liter of Purified Water under stirring in a mixing tank.
2. Xylitol (5 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled into unit dose vials.
7. Vials are packaged for distribution In this preparation Purified Water may be replaced by Water for Injection.

Example 12

A pharmaceutical formulation for either nasal or lung nebulization comprising:

| Component | Amount per 100 mL | Function |
| --- | --- | --- |
| Iota Carrageenan | 17.0 mg | Active Ingredient |
| Xylitol | 5.00 g | Active ingredient |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

This formulation contains 0.34 mg of iota carrageenan each 2 ml to be nebulized into both nostrils or into the lungs in a dose similar to the nasal sprays. Xylitol is formulated at 5.0%.

A pharmaceutical formulation was manufactured in the following way to manufacture 100 L of bulk solution, yielding ca. 3,200 multidose 30-mL bottles (an overfill is needed to obtain 10 mL extractable volume):

1. Iota Carrageenan (17.0 g) is dissolved in 90 Liter of Purified Water under stirring in a mixing tank.
2. Xylitol (5 kg) is added and dissolved under stirring
3. Potassium Sorbate (0.20 kg) is added and dissolved under stirring
4. Disodium Edetate (0.10 kg) is added and dissolved under stirring.
5. Either HCl or NaOH is added to reach pH between 6 and 7.5
6. The solution is brought to volume with additional Purified Water
7. The solution is filled into multidose bottles
8. Bottles are packaged for distribution Example 13

A pharmaceutical formulation for either nasal or lung nebulization comprising:

| Component | Amount per 100 mL | Function |
|---|---|---|
| Iota Carrageenan | 17.0 mg | Active Ingredient |
| Xylitol | 0.50 g | Active ingredient |
| NaCl | 0.81 g | Osmolyte |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

This formulation contains 0.34 mg each 2 ml to be nebulized into both nostrils or into the lungs in a dose similar to the nasal sprays. Xylitol and NaCl are formulated at 0.50% and 0.81% w/v.

A pharmaceutical formulation was manufactured in the following way to manufacture 100 L of bulk solution, yielding ca. 8,800 10-mL nasal sprays (an overfill is needed to obtain 10 mL extractable volume):

1. Iota Carrageenan (17.0 g) is dissolved in 90 Liter of Purified Water under stirring in a mixing tank.
2. Xylitol (5 kg) is added and dissolved under stirring
3. NaCl (0.81 kg) is added and dissolved under stirring
4. Potassium Sorbate (0.20 kg) is added and dissolved under stirring
5. Disodium Edetate (0.10 kg) is added and dissolved under stirring.
6. Either HCl or NaOH is added to reach pH between 6 and 7.5
7. The solution is brought to volume with additional Purified Water
8. The solution is filled into multidose bottles
9. Bottles are packaged for distribution Example 14

A pharmaceutical formulation for nasal lavage or nasal wash:

| Component | Amount per 100 mL | Function |
|---|---|---|
| Iota Carrageenan | 100.0 mg | Active Ingredient |
| Xylitol | 5.00 g | Active ingredient |
| HCl/NaOH | s.q. pH 5-7.5 | pH adjustment agents |
| Water | s.q. 100 mL | Vehicle |

This formulation contains 2 mg each 2 ml to be used as a nasal rinse. Xylitol is formulated at 5%.

This formulation was manufactured in the following way to manufacture 100 L of bulk solution, yielding ca. 1,500 60-mL units in multidose sprays or pressurized aerosols (an overfill is needed to obtain 3 mL extractable volume):

1. Iota Carrageenan (100 g) is dissolved in 90 Liter of Purified Water under stirring in a mixing tank.
2. Xylitol (5 kg) is added and dissolved under stirring
3. Either HCl or NaOH is added to reach pH between 6 and 7.5
4. The solution is brought to volume with additional Purified Water
5. The final solution is sterilized by filtration using a suitable filtration device.
6. Sterile solution is aseptically filled either into multidose spray bottles or aerosol cans.
7. In case of spray bottles a suitable pump is crimped, snapped or screw capped onto the. In the case of aerosol cans a suitable continuous spray valve is crimped onto it.

In this preparation Purified Water may be replaced by Water for Injection.

Example 15

A pharmaceutical formulation for nasal lavage or nasal wash:

| Component | Amount per 100 mL | Function |
|---|---|---|
| Iota Carrageenan | 12.0 mg | Active Ingredient |
| Xylitol | 5.00 g | Active ingredient |
| Potassium Sorbate | 0.20 g | Preservative |
| Disodium Edetate | 0.10 g | Chelating agent |
| HCl/NaOH | s.q. pH 5-7.5 | pH adjustment agents |
| Water | s.q. 100 mL | Vehicle |

This formulation was manufactured in the following way to manufacture 100 L of bulk solution, yielding ca. 1,500 60-mL units in multidose sprays or pressurized aerosols (an overfill is needed to obtain 3 mL extractable volume):

1. Iota carrageenan (12.0 g) is dissolved in 90 Liter of Purified Water under stirring in a mixing tank.
2. Xylitol (5 kg) is added and dissolved under stirring
3. Potassium Sorbate (0.20 kg) is added and dissolved under stirring
4. Disodium Edetate (0.10 kg) is added and dissolved under stirring.
5. Either HCl or NaOH is added to reach pH between 6 and 7.5
6. The solution is brought to volume with additional Purified Water
7. In case of spray bottles a suitable pump is crimped, snapped or screw capped onto the top. In the case of aerosol cans a suitable continuous spray valve is crimped onto it.

Example 16

Candidate formulations for nasal sprays to prevent transmission and alleviate symptoms and reduce viral load at an early stage of COVID 19

| Component | Amount per 100 mL | Function |
|---|---|---|
| Iota Carrageenan | 170 mg | Active Ingredient |
| NaCl | 0.90 g | Active ingredient |
| HCl/NaOH | s.q. pH 6-7 | pH adjustment agents |
| Water | s.q. 100 mL | Vehicle |

Dose to be applied 100 µL in each nostril each 4 hours or prior to exposure to COVID 19 patients (i.e. 170 µg of iota Carrageenan in each nostril)

| Component | Amount per 100 mL | Function |
|---|---|---|
| Iota Carrageenan | 120 mg | Active Ingredient |
| NaCl | 0.50 g | Active ingredient |
| HCl/NaOH | s.q. pH 6-7 | pH adjustment agents |
| Water | s.q. 100 mL | Vehicle |

Dose to be applied 140 µL or 100 µL in each nostril each 4 hours or prior to exposure to COVID 19 patients (i.e. 168 µg or 120 µg of iota Carrageenan in each nostril)

| Component | Amount per 100 mL | Function |
|---|---|---|
| Iota Carrageenan | 170 mg | Active Ingredient |
| Xylitol | 5 g | Active ingredient |
| HCl/NaOH | s.q. pH 6-7 | pH adjustment agents |
| Water | s.q. 100 mL | Vehicle |

Dose to be applied 100 µL in each nostril each 4 hours or prior to exposure to COVID 19 patients (i.e. 170 µg of iota Carrageenan in each nostril)

| Component | Amount per 100 mL | Function |
|---|---|---|
| Iota Carrageenan | 120 mg | Active Ingredient |
| Xylitol | 5 g | Active ingredient |
| HCl/NaOH | s.q. pH 6-7 | pH adjustment agents |
| Water | s.q. 100 mL | Vehicle |

Dose to be applied 140 µL or 100 µL in each nostril each 4 hours or prior to exposure to COVID 19 patients (i.e. 168 µg or 120 µg of iota Carrageenan in each nostril)

| Component | Amount per 100 mL | Function |
|---|---|---|
| Iota Carrageenan | 170 mg | Active Ingredient |
| NaCl | 0.90 g | Active ingredient |
| Potassium Sorbate | 0.20 g | Preservative |
| Disodium Edetate | 0.10 g | Chelating agent |
| HCl/NaOH | s.q. pH 5-6 | pH adjustment agents |
| Water | s.q. 100 mL | Vehicle |

Dose to be applied 100 µL in each nostril each 4 hours or prior to exposure to COVID 19 patients (i.e. 170 µg of iota Carrageenan in each nostril)

Example 17

Certain formulations described herein comprise 0.01-0.5% w/v iota Carrageenan alone or 0.001-0.5% w/v iota Carrageenan+0.5-10% w/v Xylitol. The formulations are delivered to a subject in 50-200 microliters of formulation per shot.
This would mean:
One shot of iota Carrageenan alone formulation would contain:
5 micrograms of iota Carrageenan (0.01% and 50 microliter) to 1000 micrograms or 1 mg of iota Carrageenan (0.5% and 200 microliter)
One shot of iota Carrageenan+Xylitol would contain:
0.5 micrograms of iota Carrageenan (0.001% and 50 microliter) to 1000 micrograms or 1 mg of iota Carrageenan (0.5% and 200 microliter).
250 micrograms of Xylitol (0.5% and 50 microliter) to 20 mg (5% and 200 microliter) Each application is one shot in each nostril, i.e. that the dose is double these amounts as follows:
Two shots of iota Carrageenan alone formulation would contain:
10 micrograms of iota Carrageenan (0.01% and 50 microliter) to 2000 micrograms or 2 mg of iota Carrageenan (0.5% and 200 microliter).
Two shots of iota Carrageenan+Xylitol would contain:
1 microgram of iota Carrageenan (0.001% and 50 microliter) to 2000 micrograms or 2 mg of iota Carrageenan (0.5% and 200 microliter).
500 micrograms of Xylitol (0.5% and 50 microliter) to 40 mg (5% and 200 microliter).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A nasal solution comprising a composition consisting of about 0.001% w/v to about 0.50% w/v iota carrageenan and about 0.5% w/v to about 5% w/v of xylitol as active agents, and one or more of osmolytes, buffers and combinations thereof, wherein the nasal solution is free of sugars or sugar alcohols, wherein xylitol is the only sugar alcohol present, and is hypotonic to slightly hypertonic having an osmolality of about 100-400 mOsm/kg.

2. The nasal solution of claim 1, wherein the osmolytes is sodium chloride.

3. The nasal solution of claim 1, wherein the buffers comprise at least one of: citric acid/sodium citrate, disodium hydrogen phosphate/sodium dihydrogen phosphate, acetic acid/sodium acetate or combinations thereof.

4. The nasal solution of claim 1, wherein the nasal spray is delivered by a preservative-free metering pump delivering from about 50 microliters up to 200 microliters (µl) of the solution per puff.

5. The nasal solution of claim 1, wherein the active agents are anti-viral agents.

6. The nasal solution of claim 5, wherein the anti-viral agents treat coronavirus infections.

7. The nasal solution of claim 6, the coronavirus is SARS CoV 2.

8. A pharmaceutical composition consisting of a therapeutically effective amount of 0.01% weight/volume (w/v) to about 0.50% w/v iota carrageenan, about 0.5% w/v to about 0.9% w/v sodium chloride, osmolytes, buffers and combinations thereof, wherein the iota carrageenan is an active agent and sorbitol is excluded.

9. The pharmaceutical composition of claim 8, wherein the buffers comprise: citric acid/sodium citrate, disodium hydrogen phosphate/sodium dihydrogen phosphate, acetic acid/sodium acetate or combinations thereof.

10. The pharmaceutical composition of claim 8, wherein the pharmaceutical composition is a nasal spray and is delivered by a preservative-free metering pump delivering from about 50 microliters (µL) up to 200 µL per puff.

11. A solution for nasal or lung nebulization consisting of about 0.01% w/v to about 0.50% w/v iota carrageenan, about 0.5% w/v to about 10% w/v xylitol and at least one buffer, wherein the at least one buffer comprises at least one of: citric acid/sodium citrate, disodium hydrogen phosphate/sodium dihydrogen phosphate, acetic acid/sodium acetate or combinations thereof, and wherein the solution is delivered by a preservative-free metering pump delivering about 50 microliters (µL) up to 200 µL per puff.

12. The solution of claim 11, wherein the solution is packaged into unit dose vials or any other suitable package for an unpreserved solution for nebulization.

13. A nasal solution comprising a composition consisting of about 0.001% w/v to about 0.50% w/v iota carrageenan and about 0.5% w/v to about 4% w/v of xylitol as active agents, and one or more of osmolytes, buffers and combinations thereof, wherein the nasal solution is free of sugars and is hypotonic having an osmolality of about 100-280 mOsm/kg.

14. A nasal solution comprising a composition consisting of about 0.001% w/v to about 0.50% w/v iota carrageenan and one or more of osmolytes, buffers and combinations thereof, wherein the nasal solution is free of sugars and is hypotonic having an osmolality of about 100-280 mOsm/kg.

* * * * *